United States Patent [19]

Huitema

[11] Patent Number: 6,117,152
[45] Date of Patent: Sep. 12, 2000

[54] MULTI-FUNCTION ULTRASONIC SURGICAL INSTRUMENT

[75] Inventor: Thomas W. Huitema, Cincinnati, Ohio

[73] Assignee: Ethicon Endo-Surgery, Inc., Cincinnati, Ohio

[21] Appl. No.: 09/336,066

[22] Filed: Jun. 18, 1999

[51] Int. Cl.[7] .................................................. A61B 17/00
[52] U.S. Cl. .................................. 606/169; 604/22; 601/2
[58] Field of Search .................................. 606/1, 37, 39, 606/40, 45, 169, 170–172; 601/1, 2; 604/22

[56] References Cited

U.S. PATENT DOCUMENTS

| | | |
|---|---|---|
| 3,636,943 | 1/1972 | Balamuth . |
| 3,862,630 | 1/1975 | Balamuth . |
| 3,888,004 | 6/1975 | Coleman . |
| 3,898,992 | 8/1975 | Balamuth . |
| 5,263,957 | 11/1993 | Davison . |
| 5,318,570 | 6/1994 | Hood et al. . |
| 5,322,055 | 6/1994 | Davison et al. . |
| 5,324,299 | 6/1994 | Davison et al. . |
| 5,460,629 | 10/1995 | Shlain et al. . |
| 5,549,623 | 8/1996 | Sharpe et al. . |
| 5,665,099 | 9/1997 | Pilo et al. . |
| 5,669,922 | 9/1997 | Hood . |
| 5,776,092 | 7/1998 | Farin et al. . |
| 5,906,628 | 5/1999 | Miyawaki et al. . |

FOREIGN PATENT DOCUMENTS

| | | |
|---|---|---|
| 1-232948 | 9/1989 | Japan . |
| 8-275951 | 10/1996 | Japan . |
| WO 93/14709 | 8/1993 | WIPO .................................... 606/169 |

*Primary Examiner*—Michael Buiz
*Assistant Examiner*—William Lewis

[57] ABSTRACT

A multi-function ultrasonic surgical instrument operable to perform a number of surgical procedures including: 1) scoring of tissue to a controlled depth, 2) coaptive transection of vessels utilizing a clamping mechanism, 3) coagulation under tension with a blunt edge, 4) coaptive coagulation and ablation, and 5) tissue nibbling. The multi-function ultrasonic surgical instrument includes an elongated ultrasonic waveguide and an ultrasonic end effector at a distal end of the waveguide. The ultrasonic end effector includes a recessed ultrasonic blade extending axially along a first side of the ultrasonic end effector, a distal ultrasonic blade located at the distal end of the end effector. The multi-function ultrasonic surgical instrument further includes a sheath slideably positioned on the elongated ultrasonic waveguide, wherein the sheath may be slideably positioned to expose portions of the end effector according to the surgical procedure being conducted. and surrounds at least a portion of the elongated ultrasonic waveguide. The sheath includes a channel extending from a proximal end of the sheath to a distal end of the sheath, the channel terminating at a first opening in the distal end of the sheath and a tissue notch located in the sheath proximal to the first opening, wherein the tissue notch extends from an outer surface of the sheath to the channel.

17 Claims, 9 Drawing Sheets

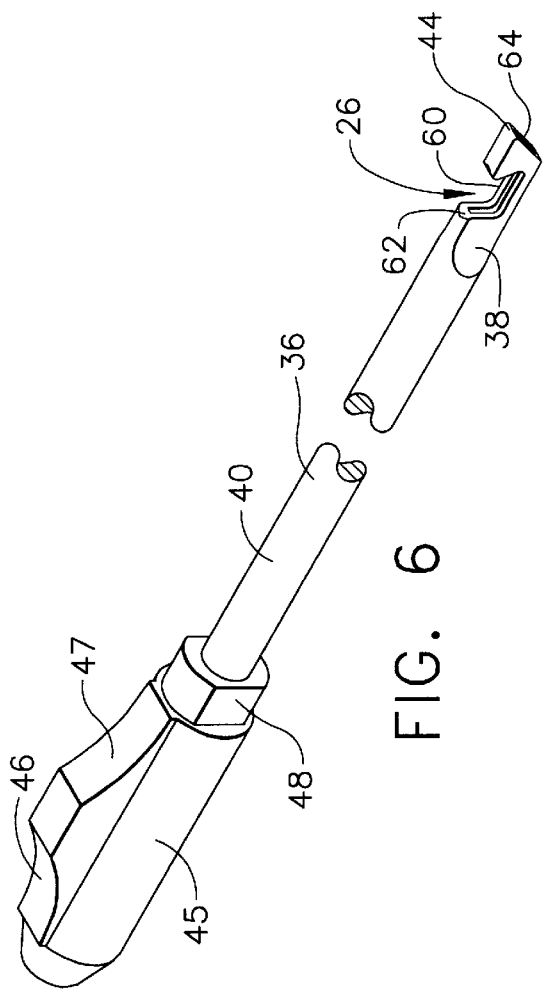
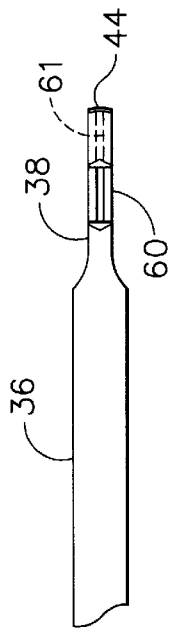
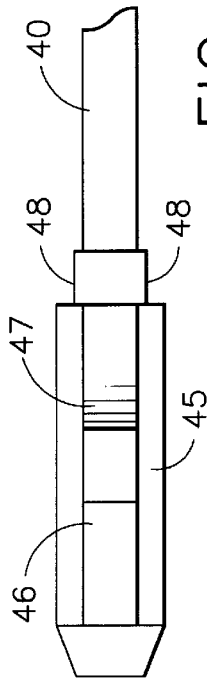
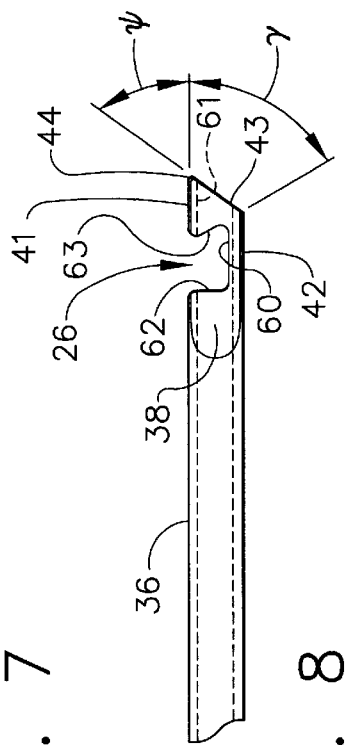
FIG. 6
FIG. 7
FIG. 8

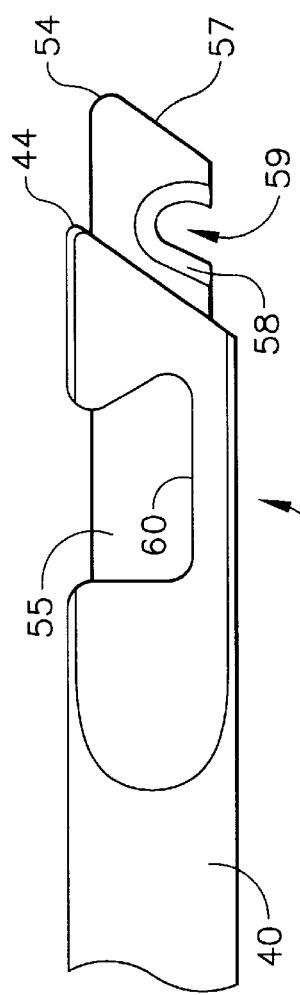
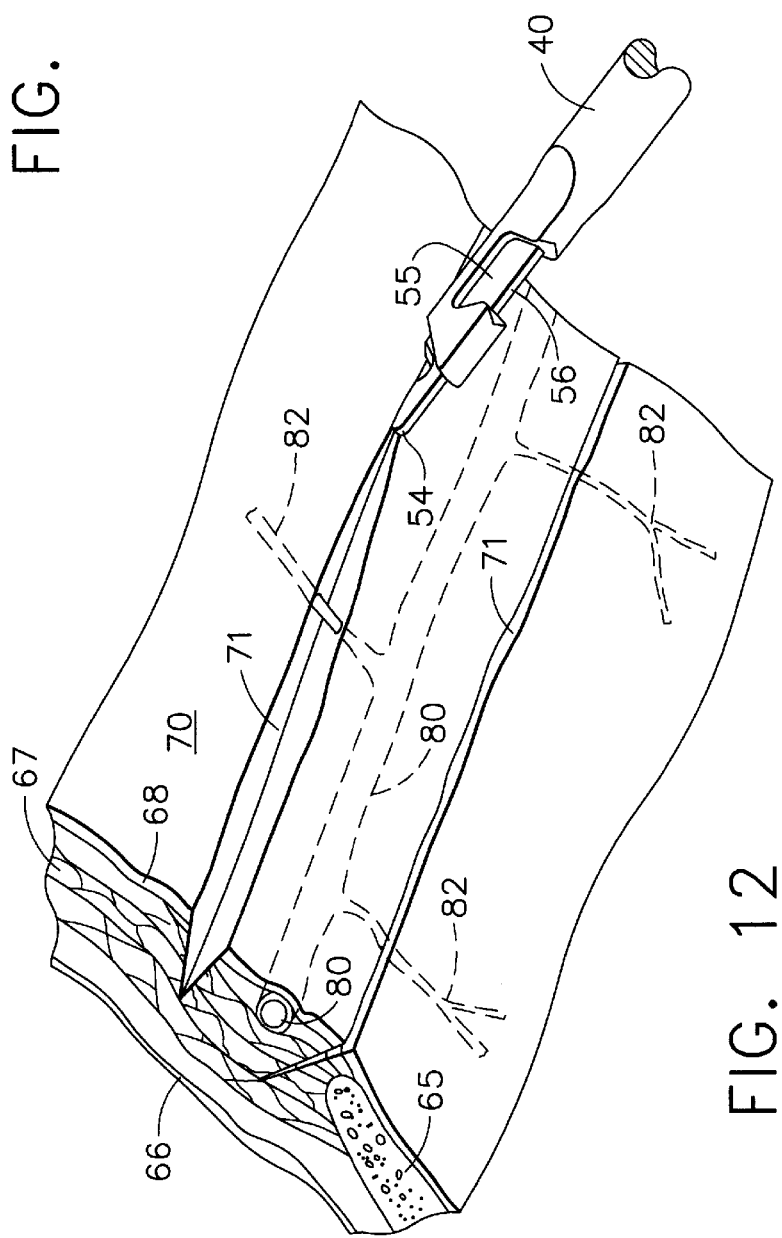

MULTI-FUNCTION ULTRASONIC SURGICAL INSTRUMENT

This application is related to the following copending patent application: U.S. application Ser. No. 08/808,652 filed Feb. 28, 1997, now U.S. Pat. No. 5,989,275, which is hereby incorporated herein by reference.

FIELD OF THE INVENTION

The present invention relates, in general, to ultrasonic surgical instruments and, more particularly, to a multi-function ultrasonic surgical instrument with an ultrasonically inactive sliding shaft encasing an ultrasonically energized blade.

BACKGROUND OF THE INVENTION

Numerous surgical procedures and instruments have been developed to replace arteries that have become blocked by disease. Coronary Artery Bypass Graft (CABG) is a form of coronary bypass surgery in which a segment from the saphenous vein is harvested and used as a bypass graft. In the CABG procedure, access to the heart is obtained via a median sternotomy in which the rib cage is split longitudinally on the midline of the chest and the left and right rib cages are spread apart. More recently surgeons have begun using a cardiac procedure known as MIDCAB (Minimally Invasive Direct Coronary Artery Bypass) in which a small, left thoracotomy (incision between the ribs on the left chest) directly above the heart is used to expose the heart.

Because of the difficulty which may be encountered when harvesting the saphenous vein, some surgeons use the Internal Mammary Artery (IMA) as an alternate graft. Use of the IMA eliminates the need for a separate leg incision while reducing the number of anastomosis to one, an anastomosis is the surgical formation of a passage between two normally distinct vessels.

The IMA is located beneath the upper rib cage, requiring the surgeon to free the IMA from the surrounding tissue before allowing the free end to be anastomosed to the coronary artery. Freeing the IMA involves cutting numerous side branch arterioles, requiring prompt hemostasis to prevent bleeding. As a result, a need has been identified for an instrument that can facilitate the severance of the IMA while providing hemostatic capabilities.

In particular, in order to mobilize the IMA in an efficient and timely manner, an appropriate surgical instrument would facilitate the following procedural steps: (1) quickly score the pleura to a shallow depth on either side of the IMA along the entire length to be mobilized; (2) dissect tissue away from the IMA side branches to isolate them for coagulation and transection; (3) coagulate and transect the side branches; and (4) provide "spot" coagulation as required with a minimal of added surgeon operations if a small bleeder is encountered during soft tissue dissection. It would, therefore, be advantageous to design a surgical instrument which facilitated most or all of the steps in the foregoing procedure.

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, or cauterize tissue. Ultrasonic instruments utilizing solid core technology are particularly advantageous because of the amount of ultrasonic energy that may be transmitted from the ultrasonic transducer through the waveguide to the surgical end effector. Such instruments are particularly suited for use in minimally invasive procedures, such as endoscopic or laparoscopic procedures, wherein the end effector is passed through a trocar to reach the surgical site. Ultrasonic instruments are also advantageous because tissue surrounding the cut line is coagulated as the instrument moves through the tissue.

Ultrasonic surgical instruments for cutting and coagulating tissue are known. Prior publications have illustrated the use of a variety of blades for various surgical applications, concentrating primarily on the cutting effect of the instrument. For example, see U.S. Pat. Nos. 3,888,004; 5,263,957; and 5,324,299. Other publications have focused on the coagulating effect such as, for example, U.S. Pat. Nos. 3,636,943; and 3,898,992, whereby coagulation is accelerated by the transfer of ultrasonic energy into the tissue, and by the heat generated from the vibratory movement of the blade. In addition, Recessed ultrasonic blades have has been used to facilitate the cutting of relatively loose and unsupported tissue such as fat where the recessed blade is drawn along the tissue allowing the blade to tension the tissue, enhancing the cutting action (see, for example, U.S. Pat. Nos. 5,669,922; and 5,324,299). Such blades work when the operator presses the ultrasonically vibrating blade directly against the tissue with sufficient pressure to effectively couple ultrasonic energy to the tissue.

As described previously, exists a need for an instrument which has a compact, guarded tip which could be used for controlled dissection as well as for coagulating and cutting functions in procedures such as, for example, the mobilization of the IMA in a MIDCAB procedure. While slidable sheaths have been used on ultrasonic surgical instruments in the past, for example to protect the ultrasonic blade, it would be advantageous to design a multifunction ultrasonic instrument including a slideable sheath wherein the sheath is a functional part of the instrument.

Accordingly, it would be advantageous to provide a multifunctional ultrasonic instrument which has a slideable sheath and a compact, guarded tip which could be used for controlled depth and heavy dissection as well as for cutting and coagulation functions. It would also be advantageous if the instrument included an ultrasonically isolated outer member or sheath, wherein the sheath could be moved axially to expose selected portions of the tip, resulting in a number of modes of operation.

In particular, it would be advantageous to provide a single ultrasonic surgical instrument which included a plurality of modes of operation including; 1) scoring of tissue to a controlled depth, 2) coaptive transection of vessels utilizing a clamping mechanism, 3) coagulation under tension with a blunt edge, 4) coaptive coagulation and ablation, and 5) tissue nibbling.

SUMMARY OF THE INVENTION

The present invention is directed to a multi-function ultrasonic surgical instrument comprising an elongated ultrasonic waveguide, an ultrasonic end effector including a plurality of ultrasonic blades at a distal end of the waveguide and a slidable sheath. In an instrument according to the present invention, the ultrasonic end effector includes a recessed ultrasonic blade extending axially along a first side of the ultrasonic end effector proximal to a distal end of the ultrasonic end effector and a distal ultrasonic blade located at the distal end of the end effector, wherein the distal ultrasonic blade extends from the first side of the ultrasonic end effector to a second side of the ultrasonic end effector. In the present invention, the slideable sheath is positioned on the elongated ultrasonic waveguide and surrounds at least a portion of the elongated ultrasonic waveguide. The sheath includes a channel extending from a proximal end of the sheath to a distal end of the sheath, the channel terminates at a first opening in the distal end of the sheath. A tissue notch is located in the sheath proximal to the first opening, wherein the tissue notch extends from an outer surface of the sheath to the channel. The sheath is slideable over a predetermined range of motion such that the distal ultrasonic blade extends from the first opening with the sheath in a first position and the distal ultrasonic blade is positioned in the tissue notch with the sheath in a second position. In one embodiment of the present invention the end effector has a cross section that is generally rectangular in shape, the first side being substantially parallel to the second side.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 6 is a fragmentary perspective view of a slideable outer sheath, according to the present invention.

FIG. 7 is a fragmentary plan view of the sheath illustrated in FIG. 6.

FIG. 8 is a fragmentary side elevational view of the sheath illustrated in FIG. 6.

FIG. 11 is a side elevational view of the end effector illustrated in FIG. 9 with the distal blade portion fully exposed according to a second functional mode of operation.

FIG. 12 is a perspective view of the end effector illustrated in FIG. 12 being utilized to excise an artery during an IMA takedown procedure.

DETAILED DESCRIPTION OF THE INVENTION

A standard ultrasonic surgical system comprises a generator that contains a power source for generating an ultrasonic frequency electrical drive signal, a handpiece containing a piezoceramic transducer for converting the electrical drive signal into mechanical vibration, and an ultrasonic surgical instrument coupled to the transducer.

Figure 1:
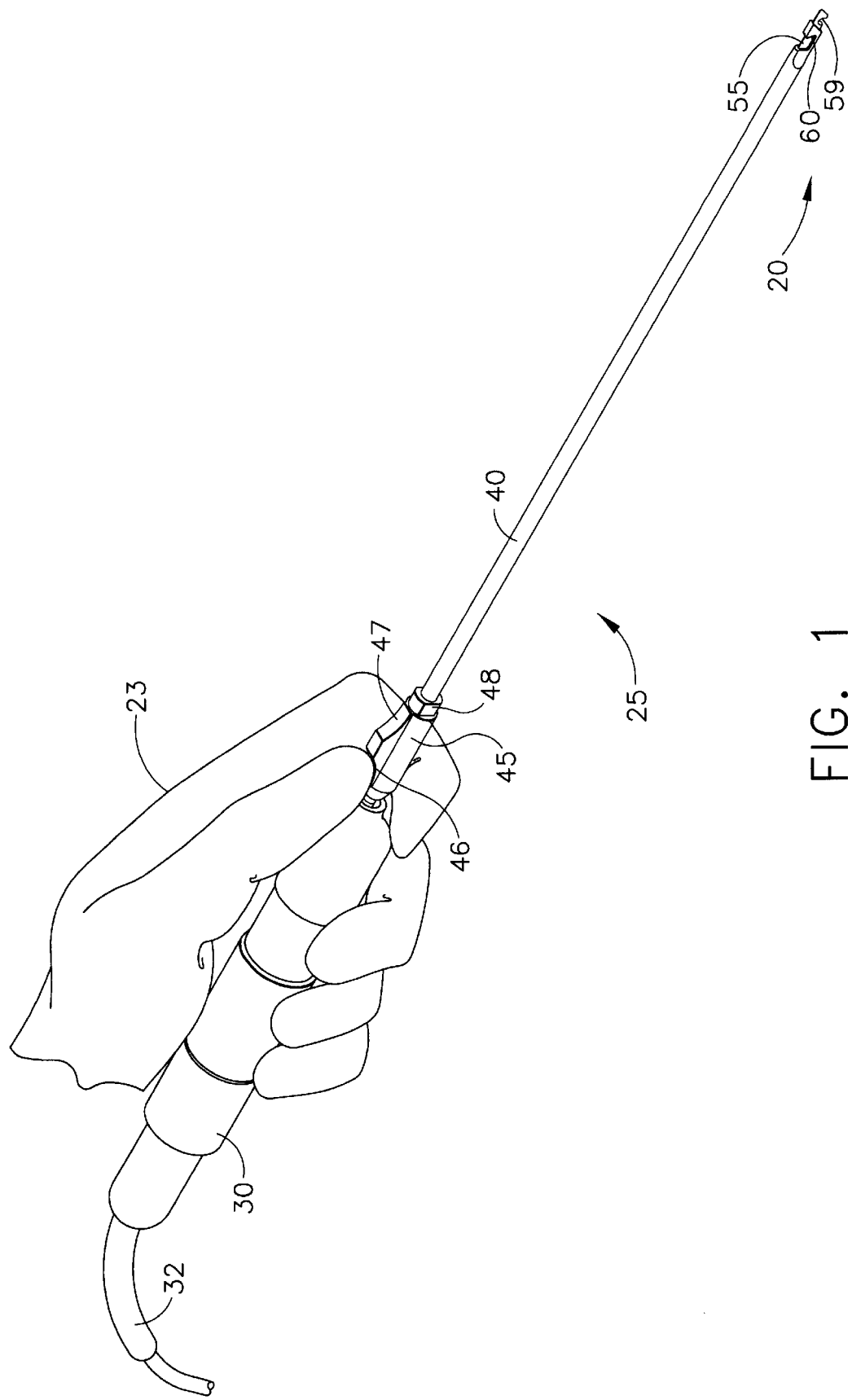
FIG. 1 is a perspective view illustrating a hand actuating a multi-function ultrasonic surgical instrument according to the present invention.

FIG. 1 is a perspective view illustrating a hand 23 actuating a multi-function ultrasonic surgical instrument 25 for vessel harvest and general use. The ultrasonic surgical instrument 25 is shown with the hand 23 grasping a transducer housing 30. Transducer housing 30 is connected via cable 32 to an ultrasonic electrical signal generator (not shown) such as the ultrasonic surgical generator available from Ethicon Endo-Surgery, Inc. as Model No. GEN01. Ultrasonic surgical instrument 25 comprises an actuation hub 45, sheath 40 and an end effector 20. Actuation hub 45 comprises a forward actuating thumb press 46, a backward actuating thumb press 47 and wrench flats 48. End effector 20 comprises a distal blade portion 55, a recessed ultrasonic blade 59, and a tissue notch 60.

Figure 2:
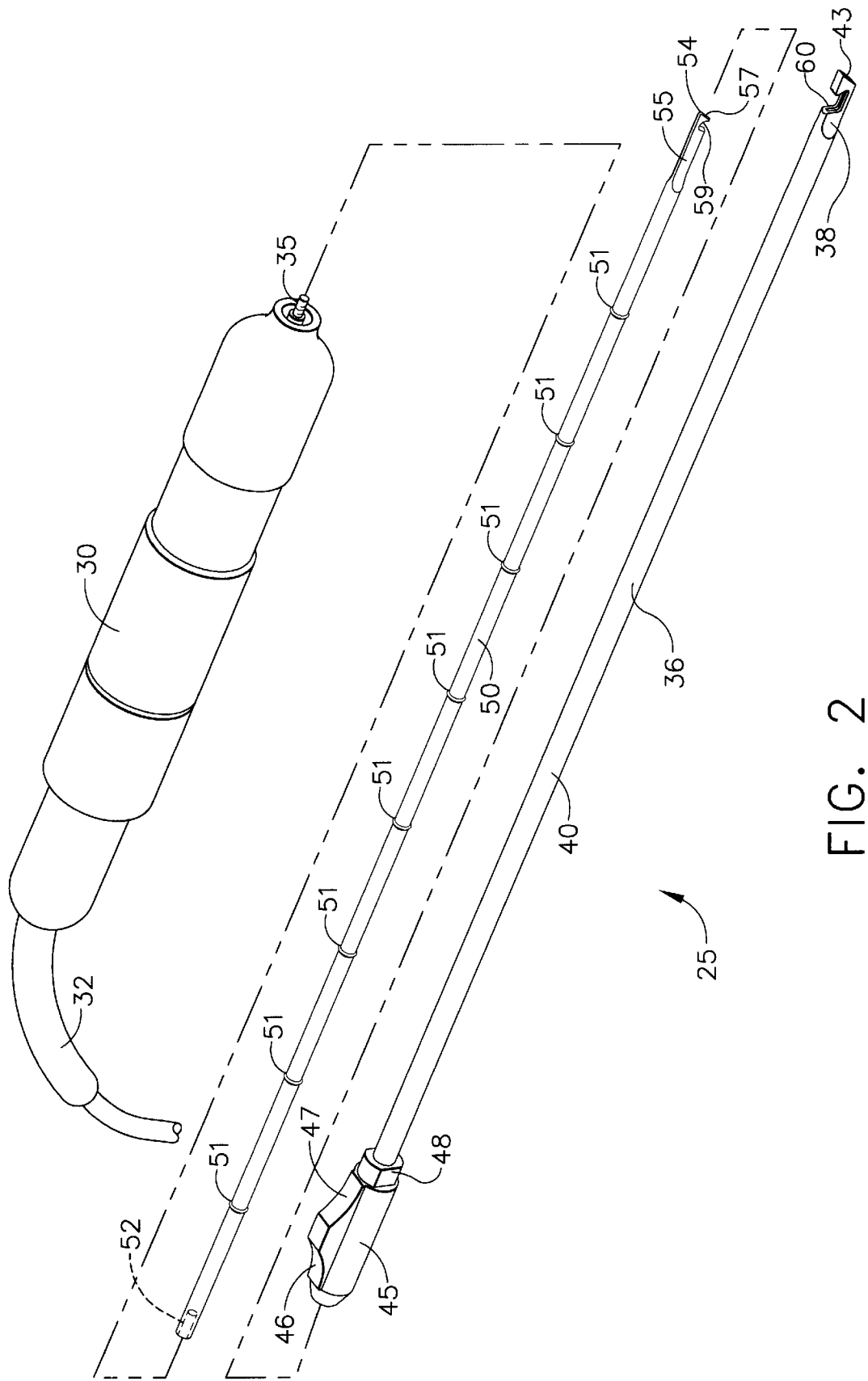
FIG. 2 is an exploded perspective view of the ultrasonic surgical instrument shown in FIG. 1.

FIG. 2 is an exploded perspective view of the ultrasonic surgical instrument 25 shown in FIG. 1. The transducer housing 30, may comprise a piezeoceramic transducer for converting an electrical signal, for example, a 55,000 Hz sinusoidal waveform, into mechanical longitudinal vibration. A connective stud 35 (made of titanium, stainless steel or other appropriate material), on the distal end of transducer housing 30, provides a connection between transducer housing 30 and ultrasonic waveguide 50. Ultrasonic surgical instrument 25 comprises ultrasonic waveguide 50 and sheath 40. Ultrasonic waveguide 50 comprises connector 52 (illustrated in this embodiment as a tapped hole capable of receiving connective stud 35), acoustic isolation elements 51, and distal blade portion 55. Distal blade portion 55 comprises recessed ultrasonic blade 59 radiused corner 54 and blade front edge 57. Sheath 40 includes hub 45, cannula 36 and blade housing 38. Hub 45 includes thumb press 46, 47 and wrench flats 48. Blade housing 38 includes tissue notch 60 and distal end face 43.

Figure 3:
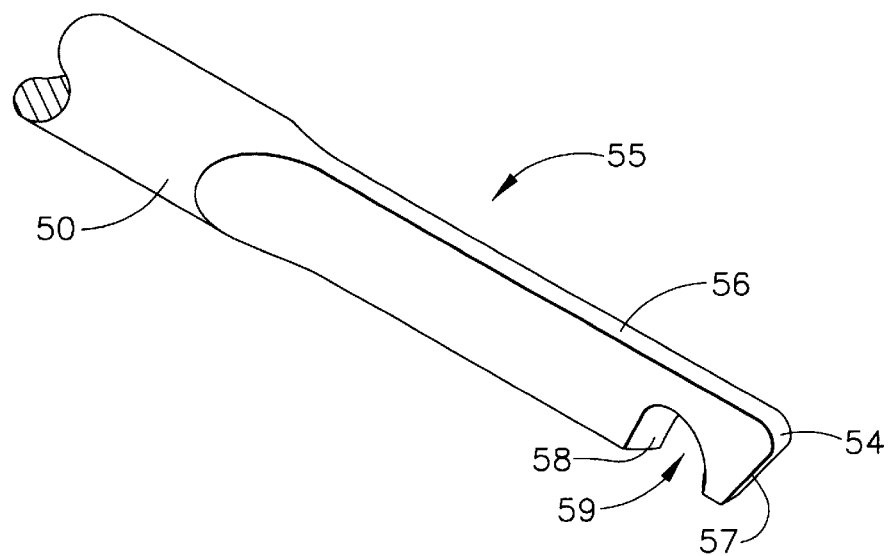
FIG. 3 is a perspective view of the distal blade portion of an ultrasonic waveguide, according to the present invention, including a recessed ultrasonic blade.
Figure 4:
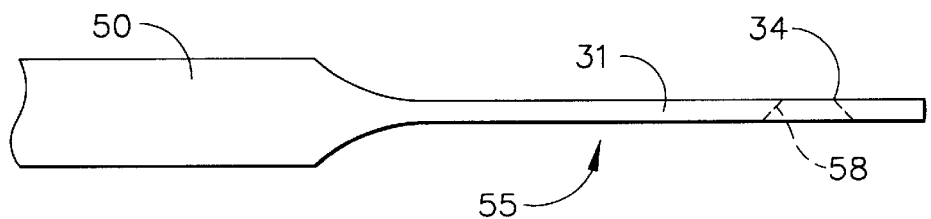
FIG. 4 is a plan view of the distal blade portion illustrated in FIG. 3.
Figure 5:
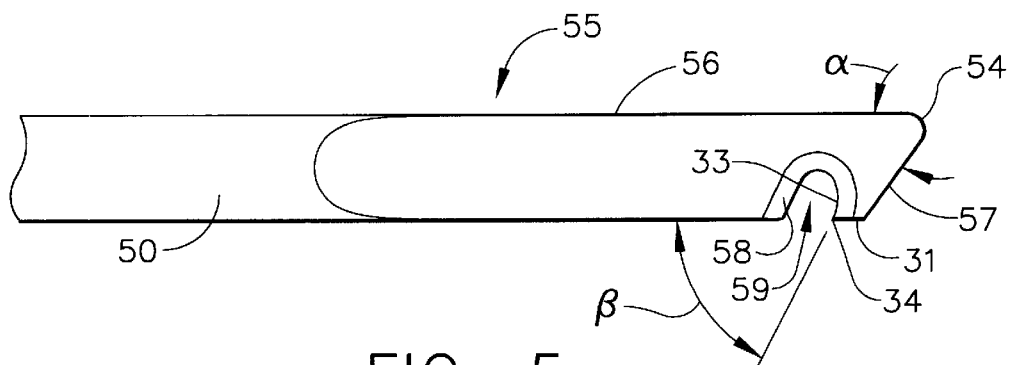
FIG. 5 is a side elevational view of the distal blade portion illustrated in FIG. 3.

FIGS. 3–5 illustrate distal blade portion 55, which is located at the distal end of ultrasonic waveguide 50. FIG. 3 is a perspective view of the distal blade portion 55 of ultrasonic waveguide 50, illustrating recessed ultrasonic blade 59 including bevel 58. FIG. 4 is a plan view of the distal blade portion illustrated in FIG. 3. Waveguide 50. The proximal end of distal blade portion 55 is radiused out to the cross-sectional shape of waveguide 50. As illustrated in FIG. 5 at the distal end of distal blade portion 55, blade second side 56 and blade front edge 57 form an acute angle α at radiused corner 54. The angle α at which blade second side 56 and blade front edge 57 meet facilitates scoring of the pleura 68 (see FIG. 10) while radiused corner 54 aids in blunt dissection. In the center of distal blade portion 55 is a recessed ultrasonic blade 59 having a bevel 58 which provides recessed ultrasonic blade 59 with sharpness when vibrating at ultrasonic frequency, as described in U.S. Pat. No. 5,263,957, the angle of cut of bevel 58 determines the sharpness of recessed ultrasonic blade 59.

FIG. 5 is a side elevational view of the distal blade portion 55 illustrated in FIG. 3. In FIG. 5 angle α is the interior angle formed by the intersection of blade second side 56 and blade front edge 57 which intersect at radiused corner 54. The use of an acute angle at the intersection of blade second side 56 and blade front edge 57 facilitates anatomical access and visualization during use of ultrasonic surgical instrument 25. In one embodiment of the present invention, α may be an angle of between approximately 30 and 80 degrees. In FIG. 5 angle β is the interior angle formed by the intersection of blade first side 31 and distal edge 33 of recessed ultrasonic blade 59 which intersect at hook point 34. The use of a hook point 34 at the distal end of recessed ultrasonic blade 59 facilitates the engagement of tissue by ultrasonic surgical instrument 25, thus, allowing ultrasonic surgical instrument 25 to pull tissue tight as it moves, which improves coupling of ultrasonic energy to the tissue.

FIGS. 6–8 illustrate sheath 40 and its components. Sheath 40 may be manufactured from polymers such as, for example, a liquid crystal polymer, or may be manufactured from metals such as, for example, stainless steel. FIG. 6 is a fragmentary perspective view of the sheath 40 illustrating the activation hub 45, cannula 36 and blade housing 38. A channel 61 runs from the proximal end of sheath 40 to the distal end of sheath 40 terminating as opening 64. Distal blade portion 55 is adapted to pass through sheath 40 protrude through opening 64. FIGS. 7 and 8 are fragmentary plan and side elevational views of the sheath 40. Channel 61 extends throughout sheath 40 to accommodate ultrasonic waveguide 50. Sheath 40 includes sheath corner 44, sheath corner 44 may be radiused and angled such that the interior angle of sheath corner 44 is equivalent to α. Tissue notch 60 includes a distal wall 63. The mouth 26 of tissue notch 60 extends from proximal face 62 to distal wall 63 creating an opening through sheath 40. As illustrated in FIG. 8, angle γ is formed by the intersection of lower side 41 with distal end face 43 at sheath corner 44. In one embodiment of the present invention, angle γ may be in the range of approximately 60 to 90 degrees. As will be apparent to those skilled in the art, the combination of an acute angle γ and an acute angle α is particularly beneficial because, as sheath 40 slides distally, blood vessels and other tissue are trapped in tissue notch 60 and forced against distal wall 63 by blade front edge 57, thus facilitating both cutting and coagulation. As illustrated in FIG. 8, angle ψ is formed by the intersection of lower side 41 with distal wall 63. In one embodiment of the present invention, angle ψ may be in the range of approximately 30 to 90 degrees. In a further embodiment of the present invention, angle ψ may be substantially equal to angle α, such that distal end face 43 is substantially parallel to blade front edge 57.

FIGS. 9–18 illustrate the use of an ultrasonic surgical instrument 25 in a number of functional applications using, as an example, IMA mobilization during a MIDCAB procedure. Using an ultrasonic instrument according to the present invention, the depth of dissection may be controlled by moving sheath 40 to expose the distal end of blade portion 55 which passes through Channel 61 and opening 64 in sheath 40. Thus, the depth of dissection increases as sheath 40 is moved distally and decreases as sheath 40 is moved proximally. Since the ultrasonic waveguide 50 remains stationary, dissection depth is determined depending on how far the sheath 40 is retracted. Blade front edge 57 is adapted to facilitate blunt dissection and coagulation of tissue and vessels positioned at the distal end of ultrasonic surgical instrument 25. Blade second side 56 facilitates the blunt dissection and coagulation of tissue and vessels positioned adjacent tissue notch 60 of ultrasonic surgical instrument 25.

Applying pressure against forward actuating thumb press 46 of actuating hub 45 with the thumb in the position illustrated in FIG. 1 causes sheath 40 to slide away from hand 23 forward, thereby protecting the distal blade portion 55. Sheath 40 may be retracted by applying force against backward actuating thumb press 47 and extended by applying force against forward actuating thumb press 46. The actuating hub 45 connects thumb press 46 and 47 to sheath 40. The actuating hub 45 is injection molded onto the sheath 40 (using delrin) and can be slid forward and backward using the forward actuating thumb press or the backward actuating thumb press allowing the distal blade portion 55 to be fully exposed, partially exposed or covered. The ultrasonic surgical instrument 25 could also be held in a tweezer-like grip in which the actuating hub 45 could be controlled using a forefinger. The ultrasonic surgical instrument 25 could be built with a range of sheath 40 lengths to cover both open and endoscopic procedures.

Recessed ultrasonic blade 59 facilitates the cutting of loose and unsupported tissue such as fat by supporting the piercing and cutting of the tissue using either a lateral or a pull-type drawing motion. The sheath 40 slidably encases the ultrasonic waveguide 50 isolating the us er from vibrations of the ultrasonic waveguide 50 and providing a number of useful modes of operations. Located along the ultrasonic waveguide 50 are vibration isolation elements 51 comprised of, for example, injection-molded silicone that isolates the ultrasonic waveguide 50 from the sheath 40. The end effector 20 is flat near the distal end to improve visibility during procedures such as endoscopic or MIDCAB procedures involving artery 80 mobilization. The sheath 40 is slideably moveable axially in relation to the ultrasonic waveguide 50 in order to achieve a number of functions desirable for optimal mobilization of, for example, the IMA.

Figure 9:
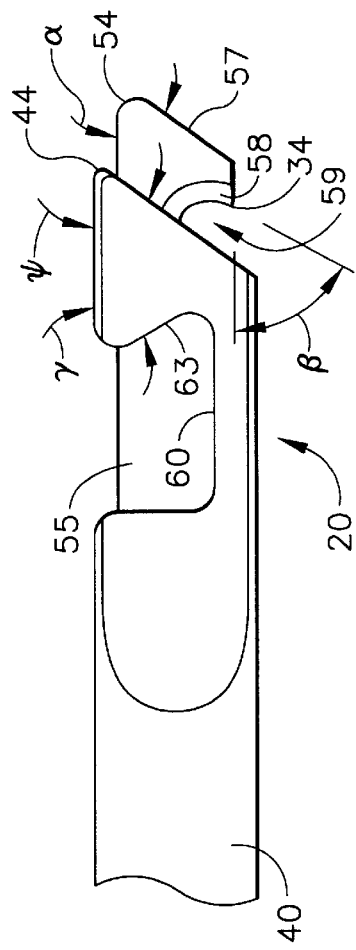
FIG. 9 is a side elevational view of an end effector, according to the present invention, with the distal blade portion partially exposed according to a first functional mode of operation.

FIG. 9 is a side elevational view of the end effector 20 including both the distal end of the sheath and the recessed ultrasonic blade, wherein the instrument is illustrated in one of its functional modes. In the functional mode illustrated in FIG. 9, sheath 40 is in a semi-retracted position wherein the distal portion of recessed ultrasonic blade 59 is exposed. Therefore, the degree to which recessed ultrasonic blade 59 may be exposed is controlled by sliding sheath 40 along ultrasonic waveguide 50. Angles α, β, γ, and ψ are also illustrated in FIG. 9.

Figure 10:
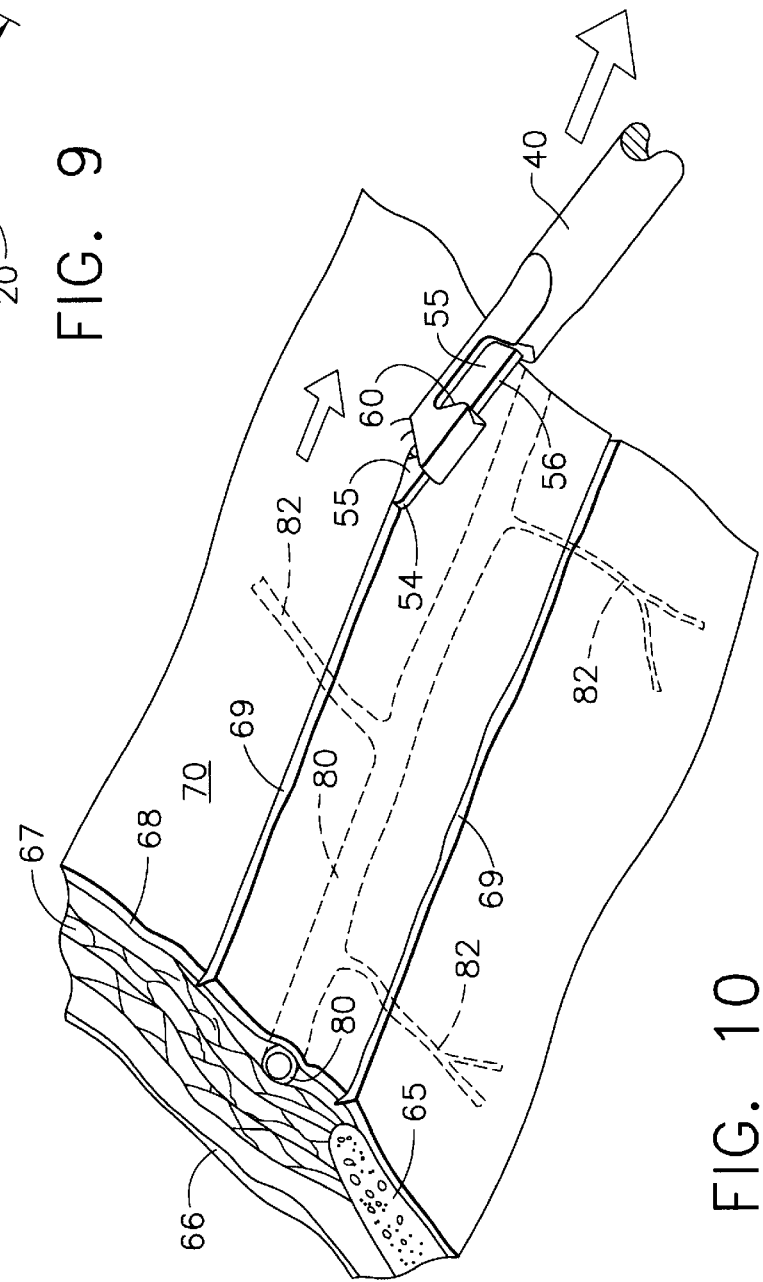
FIG. 10 is a perspective view of the end effector illustrated in FIG. 9 being utilized to score the pleura during an IMA takedown procedure.

FIG. 10 is a perspective view of the end effector being utilized, in the mode shown in FIG. 9, to score pleura 68. A surgeon may cut or score the pleura 68 on either side of an artery 80 along the full length to be mobilized. Ideally the surgeon would like an instrument capable of quickly dissecting the pleura 68 to a relatively shallow depth to expose the softer tissue and vessels beneath. As shown in FIG. 10, the surgeon can then slip the recessed ultrasonic blade 59 under the pleura 68 and quickly dissect the pleura 68 on either side of the artery 80 while the terminal portion of sheath 40 and sheath corner 44 prevents cutting too deeply and transecting an artery 80 side-branch prematurely.

Once the pleura 68 has been scored, the surgeon may blunt dissect with the ultrasonic waveguide 50 unpowered in order to mobilize the soft tissue and isolate the side branches. FIG. 11 is a side elevational view of the end effector 20 with the distal blade portion 55 fully exposed in a second functional mode. Fully exposing the recessed ultrasonic blade 59 as illustrated in FIG. 11 provides for faster ultrasonically powered or unpowered dissection.

FIG. 12 is a perspective view of the end effector being utilized, in the mode shown in FIG. 11, to excise an artery. Full extension of recessed ultrasonic blade 59 from sheath 40 provides for deeper cutting of inferior thoracic wall 70. This allows arterioles 82 to be exposed for clamping coagulation, or immediate transection. Deep incision 71 in FIG. 12 is seen to be deeper than the original scoring incision 69 shown in FIG. 10.

Figure 13:
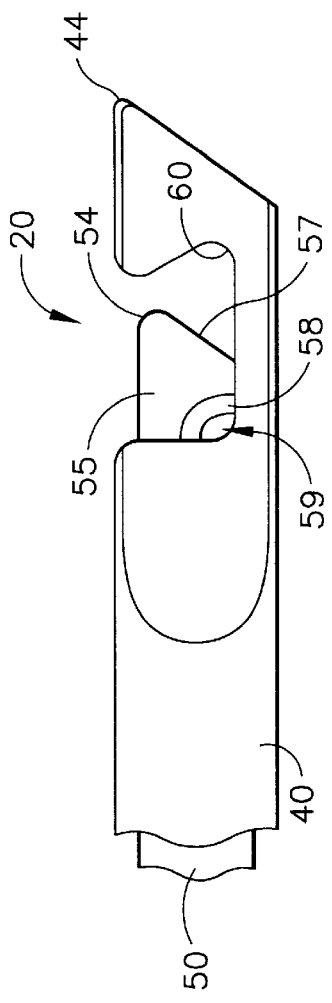
FIG. 13 is a side elevational view of the end effector illustrated in FIG. 9 with the sheath extended according to a third functional mode of operation.

Once an artery 80 side branch has been isolated, the surgeon may extend the sheath 40 by pressing along the forward actuating thumb press 46 of the actuating hub 45 as shown in FIG. 1, opening the tissue notch 60 as shown in FIG. 13. FIG. 13 is a side elevational view of the sheath extended in a third functional mode. In this position, an artery 80 side branch can be situated into the tissue notch 60 and subsequently clamp coagulated. The coagulation results from the distal portion of the distal blade portion 55 pressing against arteriole 82, clamping arteriole 82 between blade 55 and tissue notch 60, and delivering ultrasonic energy to the arteriole 82. Angle α and blade front edge 57 work in cooperation with the inverse angle of tissue notch 60, causing arteriole 82 to be drawn into ultrasonic surgical instrument 25 end effector 20 for clamping coagulation.

Figure 14:
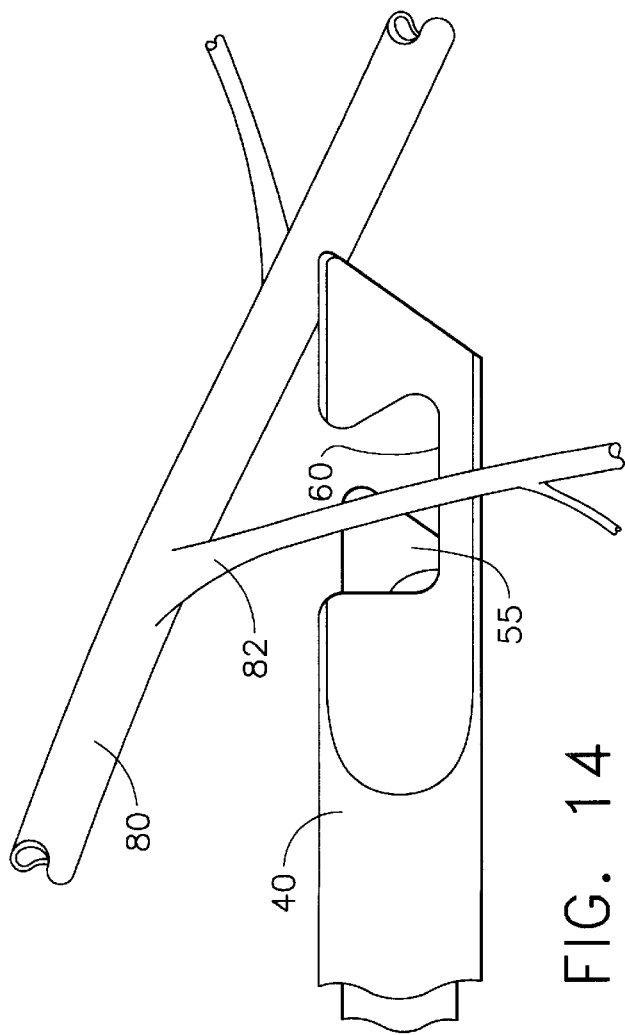
FIGS. 14–16 are side elevational views of the end effector illustrated in FIG. 13 being utilized to grasp, cut and coagulate an arteriole during an IMA take down procedure.
Figure 15:
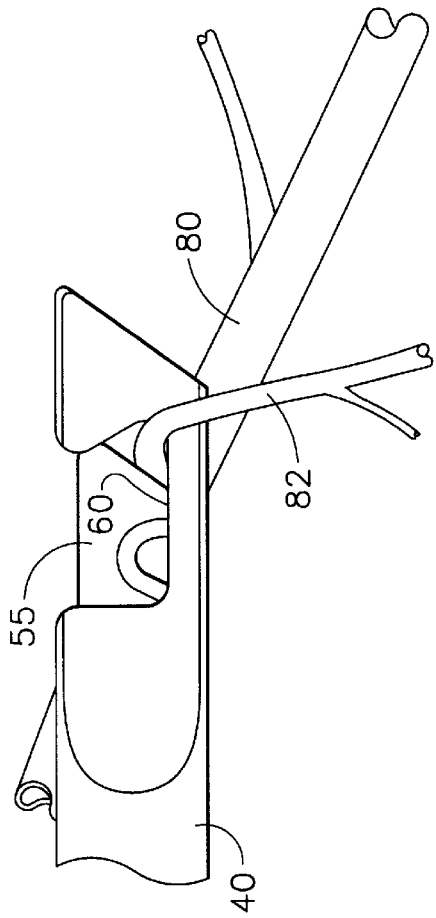
Figure 16:
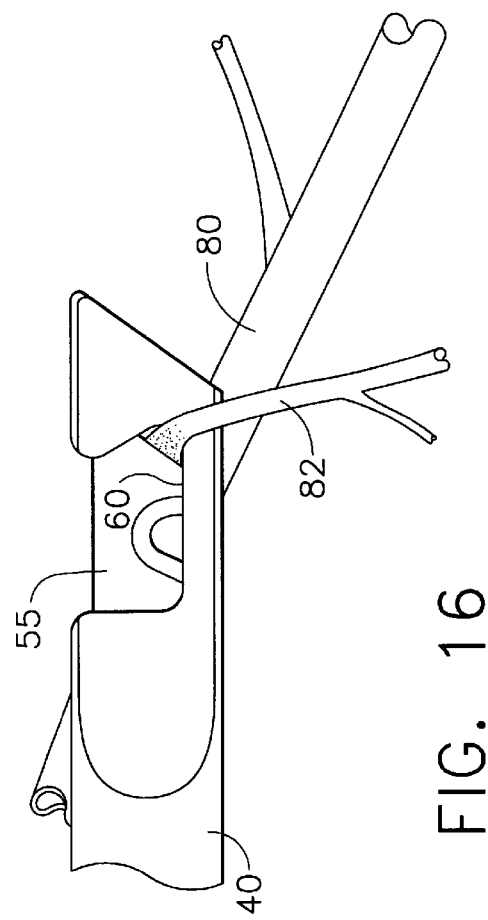

FIGS. 14–16 illustrate the use of ultrasonic surgical instrument 25 in the mode illustrated in FIG. 13. If desired, the surgeon could use this process to coagulate the arterioles 82 in one or more places, and then utilize the tissue notch 60 to cut through arterioles 82 after hemostasis is achieved. FIG. 14 is a side elevational view of the end effector 20 in the functional mode shown in FIG. 13, approaching an arteriole 82. FIG. 15 is a side elevational view of the end effector 20 in the functional mode shown in FIG. 13, clamping the arteriole 82 between the distal blade portion 55 and the sheath 40 tissue notch 60. FIG. 16 is a perspective view illustrating the end effector 20 in the mode shown in FIG. 13, clamping an artery 80 side branch arteriole 82 between the distal blade portion 55 and the tissue notch 60 of the sheath 40. Ultrasonic energy may be delivered to arteriole 82 to produce hemostasis or transection. Alternatively, larger tissue masses may be nibbled repetitively utilizing this third mode of operation.

Figure 17:
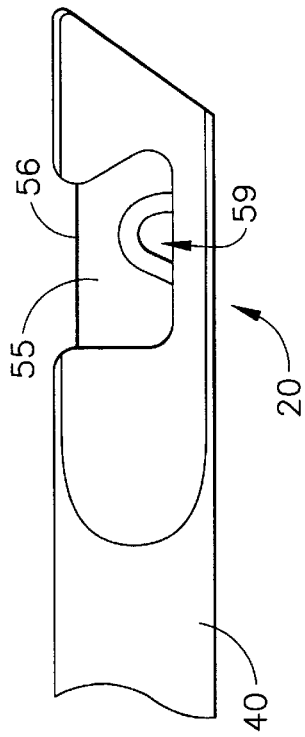
FIG. 17 is a side elevational view of the end effector illustrated in FIG. 9 with the sheath in an intermediate position according to a fourth functional mode of operation.
Figure 18:
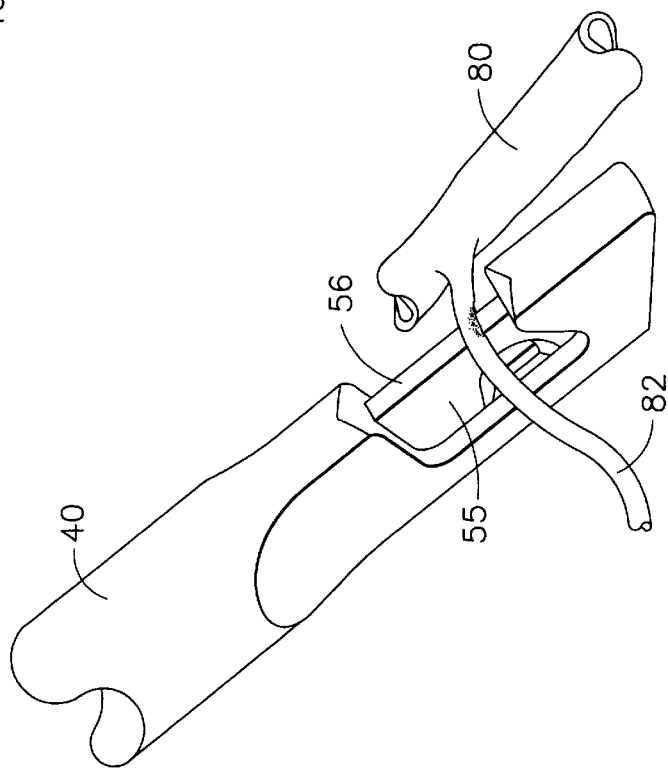
FIG. 18 is a perspective view illustrating the end effector of FIG. 17 being utilized to spot coagulate an arteriole.

FIG. 17 is a side elevational view of the end effector in fourth and fifth functional modes. Sheath 40 is positioned to locate blade front edge 57 at the terminal end of sheath 40, as illustrated in FIG. 17. This allows the use of the terminal end of end effector 20 to tamponade, and apply ultrasonic energy in a fourth functional mode, longitudinally, into tissue. FIG. 18 is a perspective view illustrating the end effector 20 being utilized in a fifth mode to spot coagulate an arteriole. At any time during the mobilization process, the surgeon may interrupt dissection and coagulate a small bleeder by using the blunt rear blade surface 56, to apply energy as shown in FIG. 18.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A multi-function ultrasonic surgical instrument comprising: an elongated ultrasonic waveguide, wherein said elongated ultrasonic waveguide comprises:

a connector at a proximal end of said waveguide;

an ultrasonic end effector at a distal end of said waveguide, wherein said ultrasonic end effector comprises:

a recessed ultrasonic blade extending axially along a first side of said ultrasonic end effector proximal to a distal end of said ultrasonic end effector;

a distal ultrasonic blade at said distal end of said end effector, wherein said distal ultrasonic blade extends from said first side of said ultrasonic end effector to a second side of said ultrasonic end effector;

a sheath slideably positioned on said elongated ultrasonic waveguide and surrounding at least a portion of said elongated ultrasonic waveguide, wherein said sheath comprises:

a channel extending from a proximal end of said sheath to a distal end of said sheath, said channel terminating at a first opening in said distal end of said sheath; and a tissue notch proximal to said first opening, wherein said tissue notch extends from an outer surface of said sheath to said channel.

2. A multi-function ultrasonic surgical instrument according to claim 1 wherein said end effector has a cross section that is generally rectangular in shape, said first side being substantially parallel to said second side.

3. A multi-function ultrasonic surgical instrument according to claim 2 wherein said distal ultrasonic blade forms an acute interior angle α with said second side.

4. A multi-function ultrasonic surgical instrument according to claim 3 wherein said recessed ultrasonic blade comprises a proximal end, a central region and a distal edge, said distal edge forming an acute interior angle β with said first side of said end effector.

5. A multi-function ultrasonic surgical instrument according to claim 4 wherein:

said central region and said distal edge of said recessed ultrasonic blade are beveled to form an ultrasonically sharp edge; and said distal ultrasonic blade is relatively blunt and includes a radiused corner where said distal ultrasonic blade intersects said second side.

6. A multi-function ultrasonic surgical instrument according to claim 1 wherein said sheath is slideable over a predetermined range of motion such that said distal ultrasonic blade extends from said first opening with said sheath in a first position and said distal ultrasonic blade is positioned in said tissue notch with said sheath in a second position.

7. A multi-function ultrasonic surgical instrument according to claim 6 wherein:

said sheath further comprises:

a proximal region;

a distal region connected to said proximal region, wherein said distal region has a cross section which is generally rectangular in shape, said distal region comprising:

an upper side;

a lower side opposite of said upper side and substantially parallel to said upper side;

said tissue notch further comprises:

a distal wall extending through said sheath to said channel and forming an acute interior angle γ with said lower side of said sheath.

8. A multi-function ultrasonic surgical instrument according to claim 7 wherein said sheath is slideably positionable over said end effector with said first side of said ultrasonic end effector adjacent said upper side of said sheath.

9. A multi-function ultrasonic surgical instrument according to claim 8 wherein said tissue notch includes a radiused recess at an end of said distal wall opposite said accute interior angle γ.

10. A multi-function ultrasonic surgical instrument according to claim 9 wherein said distal region further comprises a distal end face, said distal end face forming an acute interior angle ψ with said lower side of said sheath.

11. A multi-function ultrasonic surgical instrument according to claim 10 wherein said distal end face is substantially parallel to said distal ultrasonic blade.

12. A multi-function ultrasonic surgical instrument according to claim 10 wherein said acute interior angle ψ is from 30 to 90 degrees.

13. A multi-function ultrasonic surgical instrument according to claim 10 wherein said acute interior angle α is from 30 to 90 degrees.

14. A multi-function ultrasonic surgical instrument according to claim 10 wherein said acute interior angle γ is from 60 to 90 degrees.

15. A multi-function ultrasonic surgical instrument according to claim 10 wherein said acute interior angle ψ is from 30 to 90 degrees.

16. A multi-function ultrasonic surgical instrument according to claim 10 wherein said acute interior angle ψ is approximately equal to said acute interior angle α.

17. A multi-function ultrasonic surgical instrument according to claim 12 wherein said acute interior angle ψ is approximately equal to said acute interior angle α.

* * * * *